(12) United States Patent
Dumas et al.

(10) Patent No.: US 10,386,341 B2
(45) Date of Patent: Aug. 20, 2019

(54) CARBON DIOXIDE LIQUID PHASE FORMING USING HIGH VOLUME HEAD DISPLACEMENT

(71) Applicant: Waters Technologies Corporation, Milford, MA (US)

(72) Inventors: Robert Dumas, Upton, MA (US); Kurt D. Joudrey, Chelmsford, MA (US); Michael R. Jackson, Woonsocket, RI (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 415 days.

(21) Appl. No.: 14/898,282

(22) PCT Filed: Jun. 16, 2014

(86) PCT No.: PCT/US2014/042504
§ 371 (c)(1),
(2) Date: Dec. 14, 2015

(87) PCT Pub. No.: WO2014/204843
PCT Pub. Date: Dec. 24, 2014

(65) Prior Publication Data
US 2016/0139092 A1    May 19, 2016

Related U.S. Application Data

(60) Provisional application No. 61/836,909, filed on Jun. 19, 2013.

(51) Int. Cl.
*G01N 30/16* (2006.01)
*F04B 13/00* (2006.01)
(Continued)

(52) U.S. Cl.
CPC .......... *G01N 30/16* (2013.01); *F04B 13/00* (2013.01); *F04B 15/06* (2013.01); *F04B 15/08* (2013.01);
(Continued)

(58) Field of Classification Search
CPC .......... F04B 13/00; F04B 15/06; F04B 15/08; F04B 19/22; F04B 23/06; F04B 49/065;
(Continued)

(56) References Cited

U.S. PATENT DOCUMENTS 5,108,264 A * 4/1992 Abdel-Rahman .................... F04B 11/0075
417/20
5,158,436 A * 10/1992 Jensen ................. H02H 7/0833
417/32

(Continued)

FOREIGN PATENT DOCUMENTS

| WO | 2012122361 A2 | 9/2012 |
| WO | 2012174437 A1 | 12/2012 |
| WO | 2013134223 A1 | 9/2013 |

OTHER PUBLICATIONS

International Search Report & Written Opinion in counterpart international patent application No. PCT/US14/42504, dated Jun. 16, 2014; 20 pages.

(Continued)

*Primary Examiner* — Patrick Hamo
*Assistant Examiner* — Joseph S. Herrmann
(74) *Attorney, Agent, or Firm* — Schmeiser, Olsen & Watts LLP

(57) ABSTRACT

Systems and methods for pumping carbon dioxide in a chromatography system include an actuator that receives and compresses carbon dioxide at or above room temperature at a given pressure to put the carbon dioxide in or near (Continued)

supercritical form. This actuator can be a pre-pump disposed on the intake side of a pumping system. Alternatively, this actuator can be a primary actuator in the pumping system. The actuator includes an intake chamber that receives the carbon dioxide and a movable plunger extending into and closely received by the intake chamber. The plunger has a diameter and stroke length adapted to compress the carbon dioxide received by the intake chamber in sufficient volume at the given pressure to put the carbon dioxide in or near supercritical form at or above room temperature. A metered amount of the carbon dioxide in or near supercritical form can then be pumped.

22 Claims, 4 Drawing Sheets

(51) Int. Cl.
    *F04B 15/08*     (2006.01)
    *F04B 53/08*     (2006.01)
    *F04B 15/06*     (2006.01)
    *F04B 19/22*     (2006.01)
    *F04B 23/06*     (2006.01)
    *F04B 49/06*     (2006.01)
    *F04B 53/06*     (2006.01)
    *F04B 53/10*     (2006.01)
    *F04B 53/14*     (2006.01)
    *F04B 53/16*     (2006.01)
    *G01N 30/74*     (2006.01)
    *G01N 30/68*     (2006.01)
    *G01N 30/72*     (2006.01)
    *G01N 30/32*     (2006.01)
    *G01N 30/02*     (2006.01)
(52) U.S. Cl.
    CPC .............. *F04B 19/22* (2013.01); *F04B 23/06* (2013.01); *F04B 49/065* (2013.01); *F04B 53/06* (2013.01); *F04B 53/08* (2013.01); *F04B 53/10* (2013.01); *F04B 53/14* (2013.01); *F04B 53/16* (2013.01); *F04B 2015/0818* (2013.01); *G01N 30/68* (2013.01); *G01N 30/7206* (2013.01); *G01N 30/74* (2013.01); *G01N 2030/025* (2013.01); *G01N 2030/027* (2013.01); *G01N 2030/326* (2013.01)
(58) Field of Classification Search
    CPC .......... F04B 53/06; F04B 53/08; F04B 53/10; F04B 53/14; F04B 53/16; B01D 15/16; B01D 15/163; B01D 15/18; G01N 30/16; G01N 30/68; G01N 30/7206; G01N 30/74; G01N 2030/025; G01N 2030/027; G01N 2030/326
    USPC .................. 73/61.52, 61.56; 210/198.2, 656; 422/70; 436/161
    See application file for complete search history.

(56) References Cited

U.S. PATENT DOCUMENTS

| | | | |
|---|---|---|---|
| 5,755,559 A | 5/1998 | Allington et al. | |
| 6,071,408 A | 6/2000 | Allington et al. | |
| 6,561,767 B2 * | 5/2003 | Berger .................. | G01N 30/32 417/279 |
| 6,648,609 B2 | 11/2003 | Berger et al. | |
| 8,215,922 B2 * | 7/2012 | Berger ................ | F04B 11/0075 417/205 |
| 9,835,597 B2 * | 12/2017 | Shreve .................. | G01N 30/02 |
| 2004/0018099 A1 | 1/2004 | Berger et al. | |
| 2010/0040483 A1 * | 2/2010 | Berger ................ | F04B 11/0075 417/205 |
| 2011/0041686 A1 | 2/2011 | Monk et al. | |
| 2011/0233299 A1 | 9/2011 | Berger et al. | |
| 2011/0306146 A1 | 12/2011 | Sidhu et al. | |

OTHER PUBLICATIONS

International Preliminary Report on Patentability in counterpart PCT/US14/42504, dated Dec. 30, 2015; 13 pages.

\* cited by examiner

CARBON DIOXIDE LIQUID PHASE FORMING USING HIGH VOLUME HEAD DISPLACEMENT

RELATED APPLICATION

This application claims the benefit of and priority to U.S. provisional application No. 61/836,909, filed Jun. 19, 2013, titled "Carbon Dioxide Liquid Phase Forming using High Volume Head Displacement" the entirety of which is incorporated by reference herein.

FIELD OF THE INVENTION

The invention relates generally to chromatography systems. More specifically, the invention relates to chromatography systems that include carbon dioxide in the mobile phase.

BACKGROUND

Carbon dioxide-based chromatography systems of today (e.g., supercritical fluid chromatography or SFC) require refrigeration at their inlet pumps to ensure that the carbon dioxide ($CO_2$) is in liquid phase so that the pump can meter the $CO_2$. Conventional methods use high-cost refrigeration units to cool the $CO_2$ prior to pumping in HPLC (High Performance Liquid Chromatography) applications. Such refrigeration units often comprise thermal electric devices or refrigerated baths. These cooling devices can cause condensate to form in humid conditions on the cooled parts, such as a pump head. In many instances, the cooling devices are remote from the pump, so that the tubing between the cooling devices and the pump can form condensate. This condensate causes water drippage everywhere within cooling components, requiring huge drip trays. Condensate collection trays often succumb to bacterial growth due to long periods of standing water in trays. In addition, often the refrigerated $CO_2$ fluid is mixed with a solvent, generally methanol (or MEOH), which is at room temperature. When solvents at greatly different temperatures mix, thermal non-equilibrium effects may induce thermal errors that adversely affect separations. Additionally, pressure sensors in the pumps may overcompensate or under compensate for operating pressure, because of large temperature changes in the $CO_2$ and subsequent exposure of the $CO_2$ temperature to the pressure sensor. Other electro-mechanical devices can be sensitive to cooling temperatures and operate undesirably.

SUMMARY

In one aspect, the invention features a method for pumping carbon dioxide in a chromatography system. The method comprises receiving, at an actuator, a flow of unrefrigerated carbon dioxide. The actuator compresses a sufficient volume of the unrefrigerated carbon dioxide at a given pressure and at or above room temperature to put the carbon dioxide in or near supercritical form. A metered amount of the carbon dioxide in or near supercritical form is pumped.

In another aspect, the invention features an actuator of a pumping system used in a chromatography system. The actuator comprises an intake chamber receiving unrefrigerated carbon dioxide and a movable plunger extending into and closely received by the intake chamber. The movable plunger has a diameter and stroke length adapted to compress the unrefrigerated carbon dioxide received by the intake chamber in sufficient volume at a given pressure to put the carbon dioxide in or near supercritical form at or above room temperature.

In still another aspect, the invention features a pumping system used in a chromatography system. The pumping system comprises an actuator having an intake chamber that receives unrefrigerated carbon dioxide and a movable plunger extending into and closely received by the intake chamber. The plunger has a diameter and stroke length adapted to compress the unrefrigerated carbon dioxide received by the intake chamber in sufficient volume at a given pressure to put the unrefrigerated carbon dioxide in or near supercritical form at or above room temperature.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
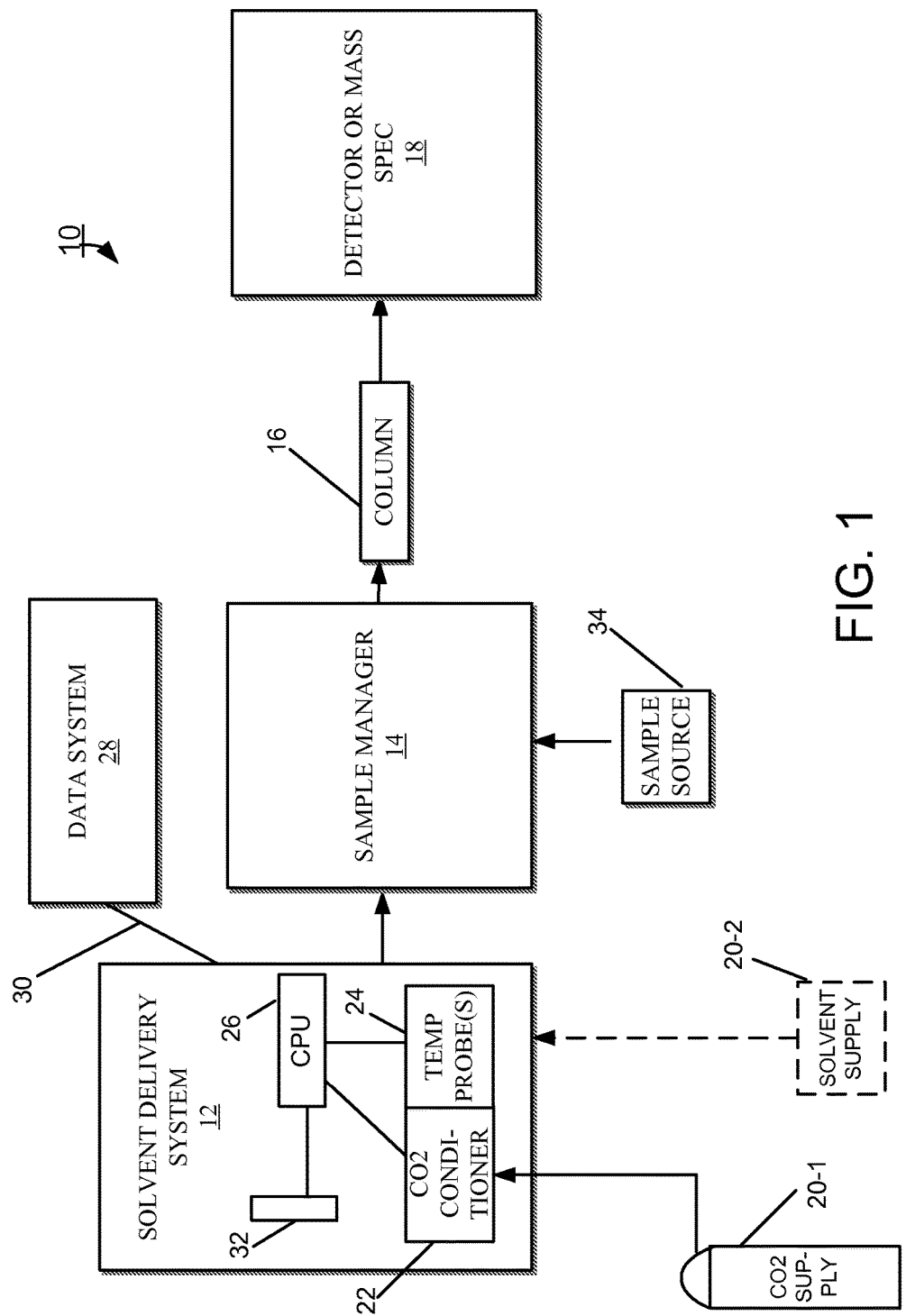
FIG. 1 is a block diagram of an embodiment of a $CO_2$-based chromatography system including a $CO_2$ conditioning apparatus.

As described herein, carbon dioxide-based chromatography systems can employ $CO_2$ for separations without requiring refrigeration. Applicants recognized they could achieve $CO_2$ densities and compressibility, without the use of refrigeration, within 5% of the densities and compressibility achieved with the use of refrigeration. Under pressure and temperature conditions described herein, the $CO_2$ can be in liquid phase, supercritical phase, or at the supercritical/liquid boundary. Use of phrases such as "in or near supercritical form", "supercritical/liquid phase," "supercritical/liquid form," and "supercritical/liquid fluid" when describing the pressurized $CO_2$ means the $CO_2$ is in liquid phase near a liquid/supercritical boundary, in or near supercritical phase, or is a blend thereof. Although $CO_2$ as a supercritical/liquid fluid has a slightly lower density than $CO_2$ as a liquid, applicants found a pump could accurately and reproducibly meter the $CO_2$ while in the supercritical/liquid form. Accordingly, unrefrigerated $CO_2$ is viable for pumping and producing reproducible sample separations. Central to this viability is to draw a sufficient volume of $CO_2$ for compression at a pressure that can achieve a density corresponding to the supercritical/liquid form.

In one embodiment, a primary actuator of a serial pump has a high volume intake chamber sized appropriately for achieving desired compression volumes. The primary actuator compresses the unrefrigerated $CO_2$ and meters the supercritical/liquid fluid. In addition, the high volume intake chamber of the primary actuator can have features designed for optimum heat transfer from the pump head to the $CO_2$ fluid in order to mitigate adiabatic heating of the $CO_2$. For example, the intake chamber can have finned geometry details to draw heat from the fluid. Other heat transfer techniques for minimizing a rise in temperature of the $CO_2$ can include, but not be limited to, optimizing the plunger stroke and/or plunger area within the intake chamber, attaching a tubing outlet to the pump head, employing heat pipe devices, heatsinks, and moving air by fan to cool the primary actuator.

Another embodiment includes a pre-pump with high pressure and high volume capabilities, which intakes unrefrigerated $CO_2$ directly in liquid or vapor form and compresses the $CO_2$ to supercritical/liquid form at, for example, 1000 psi or higher pressures and at temperatures ranging from near room temperature (e.g., 15° C.) up to approximately 40° C. The pre-pump delivers the compressed, unrefrigerated $CO_2$ as a supercritical/liquid fluid to a primary actuator of a serial pump, which meters the amount of compressed $CO_2$ delivered by a plunger stroke. The high volume ratios and high pressure ratios achievable by the pre-pump allow the pumping system of a chromatography system to pump $CO_2$ reliably for separations at room temperature. The heat transfer techniques described in connection with the previous embodiment of the primary actuator can be similarly employed with the pre-pump.

In addition, temperature probes can measure the temperature of the $CO_2$ fluid before, during, and after compression. An inlet temperature probe in thermal communication with the CO2 fluid in the intake chamber (of the primary actuator or of the pre-pump, depending on the particular embodiment) can provide temperature measurements used to determine the amount of pressure needed from a compression stroke to achieve the desired supercritical/liquid form. An outlet temperature probe disposed downstream of an accumulator actuator can serve to improve accuracy and precision of the $CO_2$ volumetric (or mass) flow rate. Temperature measurements acquired by the outlet temperature probe can serve as an index into a $CO_2$ flow lookup table, which maps temperatures to flow rates. This outlet temperature probe and lookup table enable adjustments to variations in the flow rate that result from variations in mass density caused by changes in the $CO_2$ temperature and pressure.

FIG. 1 shows an embodiment of a $CO_2$-based chromatography system 10 for separating a sample into its constituents. The chromatography system 10 includes a solvent delivery system 12 in fluidic communication with a sample manager 14 (also called an injector or autosampler) through tubing. The sample manager 14 is in fluidic communication with a chromatography separation column 16. A detector 18, for example, a mass spectrometer, can be in fluidic communication with the column 16 to receive its output.

The solvent delivery system 12 includes pumps (e.g., 100-1, 100-2 of FIG. 3) in fluidic communication with one or more solvent (or fluid) tanks or reservoirs 20-1, 20-2 (generally, 20) from which the pumps draw solvents through tubing during the course of a chromatographic run. One of the solvent reservoirs 20-1 contains a supply of $CO_2$ that is in a gaseous (vapor) state at ambient/room temperature and nominally 700 to 1000 psig. Typically, the $CO_2$ supply 20-1 maintains the $CO_2$ at an elevated pressure (e.g., 1000 psi). As described herein, the $CO_2$ can be in liquid or gaseous state at room temperature or above when delivered to the solvent delivery system 12. The other reservoir 20-2 can contain a modifier (e.g., methanol) and ternary additives (e.g., pH controllers) for mixing with the $CO_2$.

In one embodiment, the solvent delivery system 12 is a binary solvent manager (hereafter, BSM 12), which uses two individual serial flow pumps to draw solvents and to deliver a solvent composition to the sample manager 14. During operation of the BSM 12, one of the serial flow pumps draws $CO_2$ from the $CO_2$ supply 20-1, while the other serial flow pump draws another solvent from the second solvent reservoir 20-2. The mixing of solvents occurs at high pressure after the solvents pass through the pumps. An example implementation of a BSM is the ACQUITY UPLC Binary Solvent Manager, manufactured by Waters Corp. of Milford, Mass. As described herein, this mixing of $CO_2$ with a modifier or additive can occur at or above room temperature.

The $CO_2$ received from the $CO_2$ supply 20-1 passes through a $CO_2$ conditioning apparatus 22, which puts the $CO_2$ in the supercritical/liquid phase without the use of refrigeration. In brief, the $CO_2$ conditioning apparatus 22 takes in a particular volume of $CO_2$ liquid and/or gas from the $CO_2$ supply 20-1, and compresses the $CO_2$ to where the density of the $CO_2$ is at least within approximately 5% of the density of the $CO_2$ in liquid phase, as described in more detail in connection with FIG. 4.

One or more temperature probes 24 can be in thermally conductive communication with the $CO_2$ fluid. One temperature probe 24 can be configured to sense the temperature of the $CO_2$ resulting from adiabatic heating as the $CO_2$ conditioning apparatus 22 compresses and holds the $CO_2$ in the supercritical/liquid phase. Another temperature probe 24 can be configured to sense the temperature of the $CO_2$ fluid downstream of a pump (e.g., 100-1 of FIG. 3).

The solvent delivery system 12 further includes a processor 26 that is in communication with a processor-based data system 28 over a network connection 30 (e.g., Ethernet). From the data system 28, the processor 26 of the solvent delivery system 12 can be programmed to control the operation of the serial flow pumps, in accordance with a predetermined procedure that can respond to the temperature measured by the temperature probe(s) 24. For example, based on a measured temperature, the processor 26 can determine that a correction to the mass flow rate is warranted. Control of the mass flow rate improves mass flow rate accuracy, and repeatability or precision; notwithstanding, flow repeatability is a parameter value highly valued by chemists. To help determine the manner by which to correct the mass flow rate, the processor 26 accesses a mass flow rate table 32. This table 32 maps temperatures to mass flow rates. For example, if a measured temperature corresponds to a mass flow rate that is higher than desired, the processor 26 can alter the performance the pump system of the solvent delivery system 12 accordingly to maintain the desired mass flow rate.

Although shown in FIG. 1 to be part of the solvent delivery system 12, in some embodiments of the chromatography system 10, the $CO_2$ conditioning apparatus 22 is separate from the solvent delivery system 12, and connected thereto by tubing. This particular embodiment requires a pressure transducer to ensure preconditioning pressure is maintained within the pressure range prescribed by pump processor 26.

In brief overview, the solvent delivery system 12 draws an unrefrigerated mobile phase from the sources of solvent 20-1, 20-2 and moves the mobile phase (i.e., $CO_2$ or modified $CO_2$) to the sample manager 14. The chromatographic separation occurs under predetermined pressure conditions, which are either static or programmed dynamic pressure conditions. The solvent delivery system 12 can operate in a constant-pressure mode or in a constant-flow mode. In the constant-pressure mode, the pumps of the solvent delivery system 12 produce the system pressure in the chromatography system 10 in accordance with, for example, a density program. A pump of the solvent delivery system 12, as illustrated in FIG. 2 and FIG. 3, compresses a sufficient volume of the $CO_2$ to put the $CO_2$ into supercritical/liquid form.

The sample manager 14 is in fluidic communication with a sample source 34 from which the sample manager 14 acquires a sample (i.e., the material under analysis) and introduces the sample to the mobile phase (in supercritical/liquid form) arriving from the solvent delivery system 12. Examples of samples include complex mixtures of proteins, protein precursors, protein fragments, reaction products, and other compounds, to list but a few. From the sample manager 14, the mobile phase, which includes the injected sample, passes to and through the chromatography separation column 16. The separation column 16 is adapted to separate the various components (or analytes) of the sample from each other at different rates as the mobile passes through, and to elute the analytes (still carried by the mobile phase) from the separation column 16 at different times. Embodiments of the separation column 16 include a variety of sizes (e.g., preparative, semi-preparative, analytical, or capillary-scale packed-bed columns or open tubular columns) and a variety of preparations (e.g., in conventional metallic, fused silica, or polymeric tubes, or in metallic, ceramic, silica, glass, or polymeric microfluidic platforms or substrates of various IDs).

The detector 18 receives the separated components from the column 16 and produces an output from which the identity and quantity of the analytes may be determined. Examples of the detector 18 include, but are not limited to, a gas chromatography type detector, such as a Flame Ionization Detector (FID), a mass spectrometer and an evaporative light scattering detector.

Figure 2:
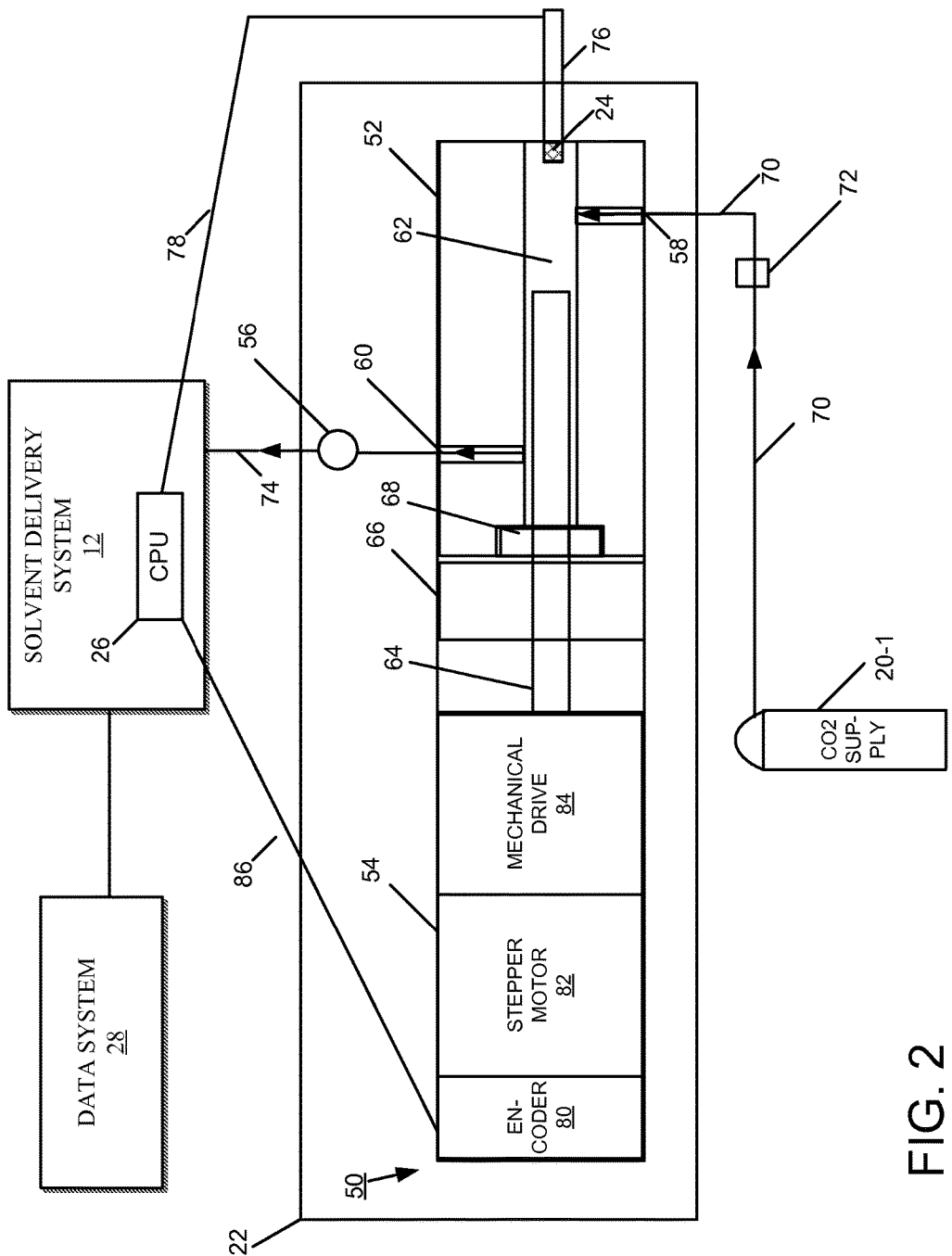
FIG. 2 is a block diagram of an embodiment of a $CO_2$ conditioning apparatus.
Figure 3:
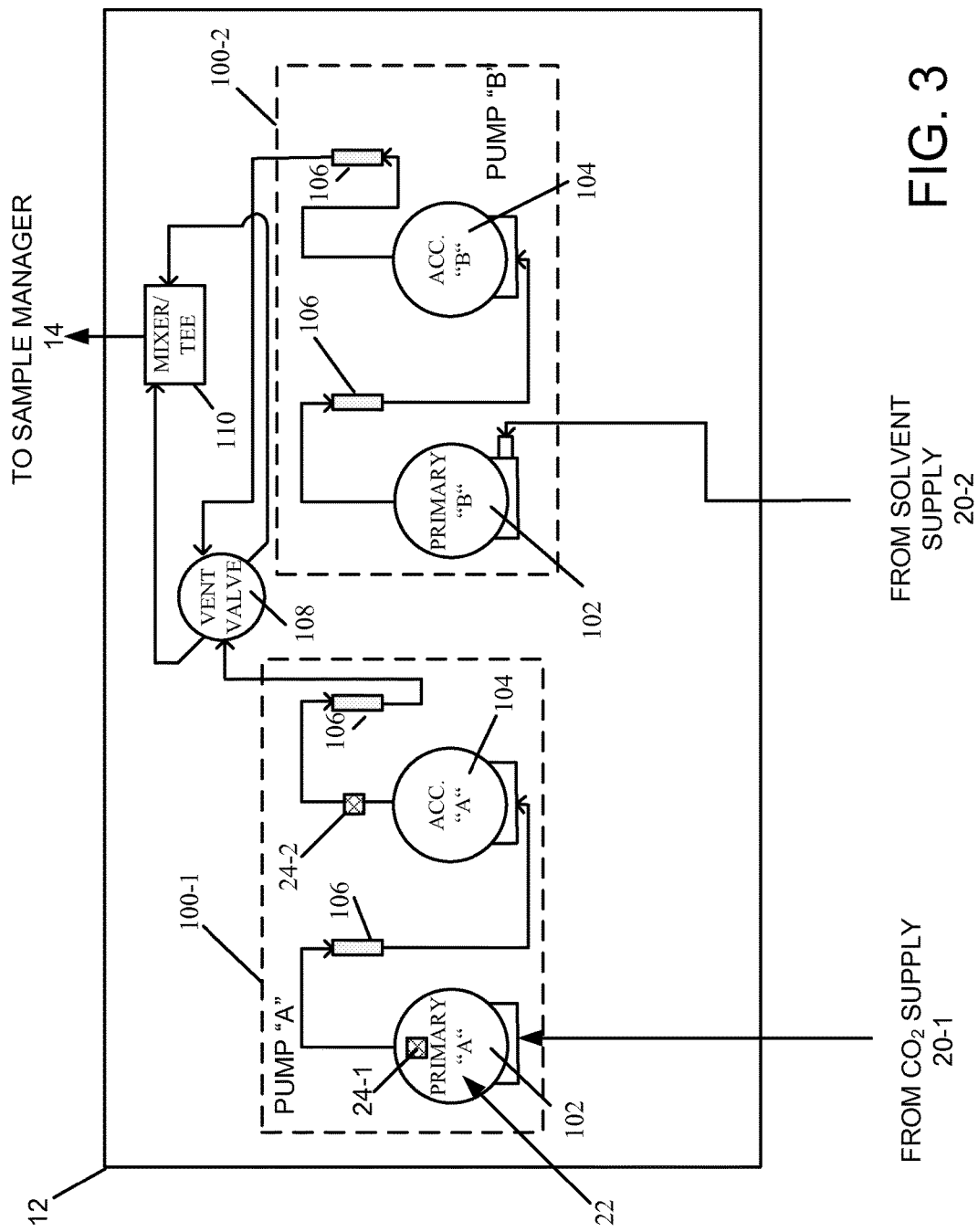
FIG. 3 is a block diagram of an embodiment of a binary solvent delivery system that includes another embodiment of the $CO_2$ conditioning apparatus.

FIG. 2 shows one embodiment of the $CO_2$ conditioning apparatus 22 of FIG. 1, including an actuator 50 having a pump head 52 and an actuator body 54. This embodiment of the $CO_2$ conditioning apparatus 22 can be referred to as a pre-pump, being disposed remotely on the intake side of the solvent delivery system 12. Coupled to an outlet side of the pump head 52 is a pressure transducer 56.

The pump head 52 includes an inlet port 58, an outlet port 60, and a fluidic chamber 62. The fluidic chamber 62 within the pump head 52 is in fluidic communication with the inlet and outlet ports 58, 60 for receiving and discharging fluids, respectively. A reciprocating plunger 64 extends into the fluidic chamber 62 through a manifold 66 and fluidic seal 68. The term "plunger" is used herein to broadly encompass plungers, shafts, rods, and pistons, whether reciprocating or rotary. Tubing 70 fluidically couples the $CO_2$ supply 20-1 to the inlet port 58 through a check valve 72. Tubing 74 also fluidically couples the outlet port 60 of the pump head 52 to the solvent delivery system 12. The arrows on the tubing 70, 74 illustrate the direction of flow of the unrefrigerated $CO_2$. A temperature probe (or sensor) 24 disposed at the tip of a metal rod 76 projects into the fluidic chamber 62, where the temperature sensor 24 measures temperature of the fluid. Link 78 abstractly illustrates a connection by which the CPU 26 acquires fluid temperatures acquired by the temperature sensor 24.

The actuator body 54 includes an encoder 80, a stepper motor 82, and a mechanical drive 84 mechanically linked to the plunger 64. The encoder 80 controls the position of the stepper motor 82, which operates the mechanical drive 84 to move the plunger 64 within the chamber 62. Signals from the CPU 26, which control the frequency and stroke length of the plunger 64, pass to the encoder 80 by way of a communication link 86, for example, a cable.

During operation of the actuator 50, a draw stroke of the plunger 64 pulls fluid (i.e., unrefrigerated $CO_2$) into the chamber 62 through the inlet port 58 and a delivery stroke of the plunger 64 pushes out of the chamber 62 through the outlet port 60. Signals from the CPU 26 control the precise operation of the plunger 64 during the draw and delivery strokes. The size of the chamber 62, and the diameter and stroke length of the plunger 64 are adapted to pull in a sufficient volume of $CO_2$ such that the compression produced by the plunger 64 can hold or transition the liquid or gaseous $CO_2$ to a supercritical/liquid phase at room (ambient) temperature (or slightly above). This compression of the $CO_2$ occurs approximately at or above 1500 psi, depending upon the liquid-to-gaseous composition of the $CO_2$ arriving from the supply 20-1; a primarily liquid flow of $CO_2$ may require less compression than a less liquid (more gaseous) flow. The pressure of the supplied $CO_2$ is another factor influencing the operation of the actuator 50; $CO_2$ arriving at the actuator 50 at 1000 psi requires less pressurization than $CO_2$ arriving at 500 psi, and can require less of a compression stroke. In addition, the temperature of the $CO_2$ measured by the temperature sensor 24 is another factor considered by the CPU 26 when controlling plunger operation; higher fluid temperatures require greater pressures to attain the supercritical/liquid state. During the delivery stroke, the plunger 64 of the actuator 50 pushes the supercritical/liquid $CO_2$ out through the outlet port 60. The supercritical/liquid $CO_2$ passes through the tubing 74 to a primary actuator of the solvent delivery system 12.

FIG. 3 shows an embodiment of the solvent delivery system 12 implemented as a binary solvent manager (hereafter, BSM 12) and configured to include the $CO_2$ conditioning apparatus 22 as described herein. The $CO_2$ conditioning apparatus 22 embodied in the BSM 12 is an alternative implementation to the pre-pump of FIG. 2.

The BSM 12 includes two pumps 100-1 and 100-2 (generally, 100), respectively labeled pump A and pump B. Each pump 100-1, 100-2 includes a primary actuator 102 and an accumulator actuator 104 coupled in series; the solvent composition stream leaving a primary actuator 102 passes through a pressure transducer 106 before arriving at the inlet of the accumulator actuator 104; and the solvent composition stream leaving an accumulator actuator 104 passes to a vent valve 108 through a pressure transducer 106.

The primary actuator 102 of the pump 100-1 is fluidically coupled to the $CO_2$ supply 20-1, which may be in a liquid or gaseous state. The primary actuator 102 of the pump 100-2 is fluidically coupled to another solvent reservoir 20-2. Each of the accumulator actuators 104 is at high pressure, maintaining the fluid received from its respective primary actuator 102 at system pressure during the intake and transfer operations performed by the primary actuator 102. In brief overview, while each primary actuator 102 intakes fluid (i.e., from the CO2 supply 20-1 or the solvent source 20-2), each accumulator actuator 104 delivers fluid at system pressure to the vent valve 108, and while each primary actuator 102 transfers fluid, the accumulator actuator 104 receives and holds the fluid at system pressure for the next delivery cycle. The high-pressure flows delivered by the accumulator actuators 104 pass through the vent valve 108 and combine at a flow-combining device 110, such as a T-section or a mixer. The solvent composition resulting from the combined flows is delivered over time to the sample manager 14.

To embody the $CO_2$ conditioning apparatus 22, the primary actuator 102 of the pump 100-1 connected to the $CO_2$ supply 20-1 is constructed and operated similarly to the actuator 50 of the pre-pump described in FIG. 2. Like the actuator 50 of FIG. 2, the primary actuator 102 of the pump 100-1 has a reciprocating plunger that extends into a chamber. The size of the chamber and the stroke length of the plunger are designed to pull in and compress a sufficient volume of $CO_2$ such that the compression produced by the plunger causes the $CO_2$ to enter a supercritical/liquid phase at room (ambient) temperature (or slightly above).

For instance, the plunger of conventional primary actuators typically has a 0.125-inch diameter and a 0.500-inch stroke length. The delivery stroke of such a plunger compresses approximately 30 µl, maximum, of carbon dioxide. Such a compression volume without refrigeration is insufficient to attain a pressure at which $CO_2$ enters supercritical/liquid form. To attain that pressure, the compression volume should be at least 8 times greater than the delivery volume compressed by the conventional primary actuator. This 8× multiplication factor implies a compression volume of at least 240 µl. To achieve this greater compression volume, the diameter and stroke length of the plunger of the primary actuator 102 can be adapted such that the plunger has twice the diameter (i.e., 0.25 inch) and twice the stroke length as the plunger of a conventional actuator. (The intake chamber of the actuator, in order to receive closely the modified plunger, is also adapted to receive the greater compression volume). Doubling the plunger diameter produces a 4× multiplication factor; doubling the stroke length produces a 2× multiplication factor; the cumulative effect of the modifications is an 8× multiplication factor. Such an actuator may thus cause $CO_2$ to enter supercritical/liquid form at or greater than 1000 psi (depending on the temperature of the $CO_2$).

The doubling of the plunger diameter and stroke length is just one example of adaptations to a plunger that can achieve an 8× multiplication factor. Various other permutations of modifications to the diameter and stroke length of plungers of conventional actuators can be performed in order to attain a sufficient compression volume, without departing from the principles described herein. Further, the 8× multiplication factor is also just an example; for instance, a 3× multiplication factor can be sufficient to cause $CO_2$ to enter supercritical/liquid form (i.e., depending upon the particular pressure and temperature of the $CO_2$). In addition, actuators embodying the principles herein can support larger compression volumes than 800 µl, for example, 1.5 ml, and accordingly use pressures lower than 1500 psi (e.g., 1000 psi) to cause $CO_2$ to enter liquid or supercritical form. Although described in connection with the primary actuator 102 of pump 100-1, these principles also extend to the actuator 50 of the pre-pump embodiment described in FIG. 2.

Like the actuator 50 of FIG. 2, the primary actuator 102 of the pump 101-1 can also have an inlet temperature probe 24-1, for measuring the temperature of the $CO_2$ and providing these temperature measurements as feedback to the CPU 26 of the solvent delivery system 12. From such temperature measurements, the CPU 26 may determine to increase the pressure produced by the primary actuator 102 in order to keep the $CO_2$ in supercritical/liquid form.

In addition, the pump 101-1 can also have an outlet temperature sensor 24-2 disposed downstream of the accumulator actuator 104. The temperature measurements provided to the CPU 26 by this outlet temperature sensor 112 provides feedback that helps control the mass flow rate. To keep the mass flow rate constant, for instance, the CPU 26 controls the performance of the accumulator actuator 104. Using the look-up table 32 (FIG. 1), the CPU 26 maps a current temperature measurement to a mass flow rate. For example, higher temperatures correspond to lesser densities, which correlate to slower mass flow rates. In response to the mass flow rate mapped to by the currently measured temperature, the CPU 26 may determine to move the plunger of the accumulator actuator 104 faster or slower, accordingly, in order to keep the mass flow rate constant. For example, if the temperature of the outlet fluid maps to a current mass flow rate that is less than the target mass flow rate, the CPU 26 can increase the speed of the plunger of the accumulator actuator 104 in order to raise the current mass flow rate to the target mass flow rate. Although described in connection with the embodiment of FIG. 3, the solvent delivery system 12 of FIG. 2 can also similarly employ an outlet temperature sensor (e.g., 24-2) to measure the fluid temperature downstream of an accumulator actuator for purposes of controlling the mass flow rate produced by the pumps.

Figure 4:
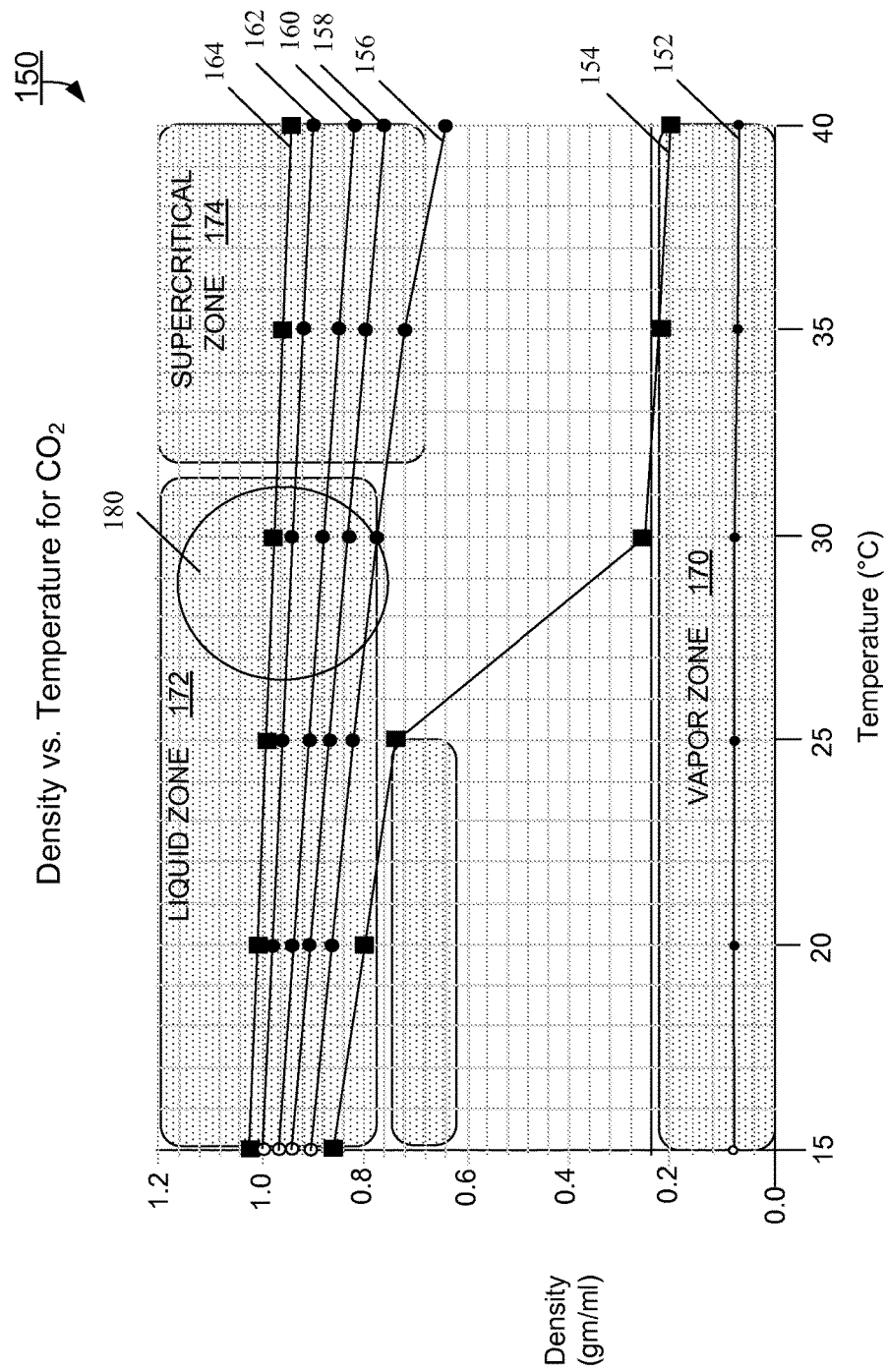
FIG. 4 is a plot of density versus temperature for $CO_2$ at different pressures.

FIG. 4 shows a plot 150 of various operating curves 152, 154, 156, 158, 160, 162, and 164, each curve plotting density (gms/ml) versus temperature for $CO_2$ at a specific pressure. The range of temperatures for the operating curves is 15° C. to 40° C. The compressed volume of $CO_2$ is about 1 ml. The plot 140 includes general outlines for a vapor zone 170, a liquid zone 172, and a supercritical zone 174. Each zone corresponds to a different form or state of the carbon dioxide: for example, carbon dioxide is in liquid form in the liquid zone 172 and in supercritical form in the supercritical zone 174.

The operating curve 152 corresponds to $CO_2$ compressed at 500 psi. The curve 150 shows the density of the carbon dioxide remaining relatively unchanged across the temperature range. In addition, the carbon dioxide is in the vapor zone 170 throughout the temperature range.

The operating curve 154 corresponds to compressing $CO_2$ at 1000 psi. At temperatures at or near room temperature (15° C.-25° C.), the curve 154 shows the $CO_2$ to be in the liquid zone 172. Above 25° C., the curve 154 drops off sharply, with the $CO_2$ moving towards and into the vapor zone 170. This curve 154 demonstrates the viability of compressing $CO_2$ at room temperatures, although temperatures greater than room temperature cause the $CO_2$ to be in vapor form, which cannot be reliably metered for purpose of sample separations. Accordingly, compression at 1000 psi requires strict temperature controls and effective heat transfer mechanisms to ensure the temperature of the $CO_2$ remains near or at room temperature and, consequently, in liquid form.

The operating curve 156 corresponds to $CO_2$ compressed at 1500 psi. At this pressure, the carbon dioxide remains in the liquid zone 172 up to approximately 30° C. Above 30° C., the operating curve 156 passes through the liquid/supercritical boundary into the supercritical zone 174, falling slightly below (outside of) the supercritical zone 174 at 40° C. This operating curve 156 represents acceptable density and pressure conditions for conditioning the $CO_2$ (i.e., holding the $CO_2$ in a form suitable for accurate metering).

The operating curves 158, 160, 162, and 164 correspond to pressures of 2000 psi, 3000 psi, 4000 psi, and 5000 psi, respectively. For each of these curves 158, 160, 162, and 164, the $CO_2$ is in the liquid zone 172 across the temperature range of 15° C.-25° C. to approximately 30° C., and in the supercritical zone 174 for the remainder of the disclosed temperature range (i.e., up to 40° C.). These operating curves 158, 160, 162, and 164 demonstrate other acceptable pressure and density conditions for purposes of conditioning the $CO_2$. Of the operating curves 154, 156, 158, 160, 162, and 164, the operating curve 164 (5000 psi) represents the most consistent production of $CO_2$ in a liquid/supercritical form across the disclosed temperature range.

Conventional chromatography systems that use refrigerated $CO_2$ operate generally in the region 180 within the liquid zone 172, where the density of the $CO_2$ ranges approximately between 0.7 and 1.0 gm/ml. Compressing unrefrigerated $CO_2$, as described herein, can result in fluid temperatures that are slightly higher than room, that is, approximately 32° C. to 40° C. To operate at these temperatures within (or sufficiently near) the supercritical zone 174, the plot 150 shows the pressure should be at least 1500 psi. At pressures greater than 1500 psi and at temperatures slightly greater than room, the plot 150 shows the density of the $CO_2$ to drop from the region 180 to the supercritical zone 174 by approximately 5% to 10%. For example, at 2000 psi (curve 158), the density of $CO_2$ at 30° C. in the region 180 is 0.83, while its density at 40° C. in the supercritical zone 174 is 0.76, which is a drop of approximately 8.4%. As another example, at 4000 psi (curve 162), the density of $CO_2$ at 30° C. in the region 180 is 0.94, while its density at 40° C. in the supercritical zone 174 is 0.90, which is a drop of approximately 4.2%. Hence, at certain pressures, $CO_2$ densities and compressibility can be achieved, without the use of refrigeration, within approximately 5% of the densities and compressibility achieved with the use of refrigeration.

While the invention has been shown and described with reference to specific preferred embodiments, it should be understood by those skilled in the art that various changes in form and detail may be made therein without departing from the spirit and scope of the invention as defined by the following claims.

What is claimed is:

1. A method for pumping carbon dioxide in a chromatography system, the method comprising:
    receiving, at a fluidic chamber that is an intake chamber of an actuator of a pump, a flow of the carbon dioxide at or above room temperature;
    compressing, by a stroke of a plunger of the actuator of the pump a volume of the carbon dioxide, at a given pressure and at or above said room temperature, to within about 10% or more of the density of the carbon dioxide in liquid phase;
    metering an amount of the compressed carbon dioxide delivered by the stroke of the plunger of the actuator of the pump, wherein the chromatography system includes the pump; and
    wherein the metered amount of the compressed carbon dioxide is delivered from the pump directly to a sample manager of the chromatography system.

2. The method of claim 1, further comprising exchanging heat from the compressed carbon dioxide to a surface of the actuator to mitigate a temperature rise of the compressed carbon dioxide attributed to adiabatic heating resulting from the compression.

3. The method of claim 1, further comprising cooling the actuator to mitigate a temperature rise of the compressed carbon dioxide attributed to adiabatic heating resulting from the compression.

4. The method of claim 1, further comprising:
    measuring a temperature of the carbon dioxide within the intake chamber of the actuator; and
    adjusting the given pressure used to compress the volume of the carbon dioxide in response to the measured temperature.

5. The method of claim 1, further comprising:
    measuring a temperature of the compressed carbon dioxide within the intake chamber of the actuator; and
    cooling the actuator in response to the measured temperature.

6. The method of claim 1, wherein the given pressure for the compressing of the carbon dioxide occurs at greater than or equal to 1500 psi when a temperature of the carbon dioxide is approximately 40 degrees Centigrade.

7. The method of claim 1, wherein the received flow of the carbon dioxide is liquid, gas, or a mixture thereof.

8. The method of claim 1, further comprising mixing, at said room temperature or above, a modifier with the compressed carbon dioxide.

9. The method of claim 1, wherein the carbon dioxide is compressed to within about 5% or more of the density of the carbon dioxide in the liquid phase.

10. The method of claim 1, wherein the carbon dioxide is compressed to put the carbon dioxide in supercritical form.

11. The method of claim 1, wherein the carbon dioxide is compressed to put the carbon dioxide near supercritical form.

12. An actuator of a pumping system used in a chromatography system, the actuator comprising:
    a fluidic chamber that is an intake chamber of the actuator of a pump in the pumping system receiving carbon dioxide at or above room temperature; and
    a movable plunger extending into and closely received by the intake chamber, the movable plunger having a diameter and stroke length adapted to compress a volume of the carbon dioxide received by the intake chamber at a given pressure to within about 10% or more of the density of the carbon dioxide in liquid phase, wherein the chromatography system includes the pump; and
    wherein the plunger pumps a metered amount of the compressed carbon dioxide from the pump directly to a sample manager of the chromatography system.

13. The actuator of claim 12, further comprising a temperature probe disposed within the intake chamber to measure a temperature of the carbon dioxide being compressed by the plunger.

14. The actuator of claim 12, further comprising a temperature probe in thermal communication with the carbon dioxide being compressed by the plunger.

15. The actuator of claim 12, wherein the given pressure is greater than or equal to 1500 psi when a temperature of the compressed carbon dioxide is approximately 40 degrees Centigrade.

16. A pumping system used in a chromatography system, the pumping system comprising:
    an actuator having a fluidic chamber that is an intake chamber of a pump that receives carbon dioxide at or above room temperature and a movable plunger extending into and closely received by the intake chamber, the plunger having a diameter and stroke length adapted to compress a volume of the carbon dioxide received by the intake chamber at a given pressure to within about 10% or more of the density of the carbon dioxide in liquid phase;
    wherein the chromatography system includes the pump; and
    wherein the plunger pumps a metered amount of the compressed carbon dioxide from the pump to transport the compressed carbon dioxide directly to a sample manager of the chromatography system.

17. The pumping system of claim 16, further comprising a heat exchanger in thermal communication with the compressed carbon dioxide in the intake chamber to mitigate a temperature rise attributed to adiabatic heating.

18. The pumping system of claim 16, further comprising a temperature probe in thermal communication with the carbon dioxide being compressed by the plunger.

19. The pumping system of claim 18, further comprising:
a processor in communication with the temperature probe to receive a temperature measurement of the carbon dioxide being compressed, the processor adjusting the given pressure at which to compress the carbon dioxide in response to the temperature measurement.

20. The pumping system of claim 18, further comprising a heat exchanger in thermal communication with the carbon dioxide in the intake chamber, the heat exchanger operating to cool the carbon dioxide in response to the temperature measurement.

21. The pumping system of claim 16, wherein the given pressure is greater than or equal to 1500 psi when a temperature of the compressed carbon dioxide is approximately 40 degrees Centigrade.

22. The pumping system of claim 16, wherein the received flow of the carbon dioxide is liquid, gas, or a mixture thereof.

\* \* \* \* \*